United States Patent [19]
Veits

[11] Patent Number: 5,702,579
[45] Date of Patent: Dec. 30, 1997

[54] PROCESS FOR MAKING ASCORBIC ACID

[75] Inventor: Joachim Veits, Rheinfelden, Germany

[73] Assignee: Roche Vitamins Inc., Paramus, N.J.

[21] Appl. No.: 766,695

[22] Filed: Dec. 13, 1996

[30] Foreign Application Priority Data

Dec. 14, 1995 [CH] Switzerland ............................ 3540/95

[51] Int. Cl.$^6$ ................................................. B01D 61/44
[52] U.S. Cl. ..................... 204/522; 204/529; 204/530; 204/534; 204/537; 204/541
[58] Field of Search ................................ 204/522, 529, 204/530, 534, 537, 541

[56] References Cited

U.S. PATENT DOCUMENTS

| | | | |
|---|---|---|---|
| 2,829,095 | 4/1958 | Oda et al. | 204/98 |
| 3,968,017 | 7/1976 | Canata et al. | 204/541 |
| 4,024,043 | 5/1977 | Dege et al. | 204/296 |
| 4,057,483 | 11/1977 | Giuffrida | 204/301 |
| 4,082,835 | 4/1978 | Chlanda et al. | 423/242 |
| 4,116,889 | 9/1978 | Chlanda et al. | 521/27 |
| 4,375,393 | 3/1983 | Reiff et al. | 204/79 |
| 4,738,764 | 4/1988 | Chlanda et al. | 204/296 |
| 4,767,870 | 8/1988 | Fujiwara et al. | 549/315 |
| 4,781,809 | 11/1988 | Falcone, Jr. | 204/541 |

FOREIGN PATENT DOCUMENTS

| | | |
|---|---|---|
| 040 709 A | 12/1981 | European Pat. Off. . |
| 2 291 291 A | 6/1976 | France . |
| 3621781 | 1/1987 | Germany . |
| 111062 | 9/1975 | Japan . |
| 871 500 | 6/1961 | United Kingdom . |
| 92/11080 | 7/1992 | WIPO . |

OTHER PUBLICATIONS

Patent Abstract of Japan, vol. 012, No. 306 (C-522) (Aug. 19, 1988) of Japanese Patent No. 63077890.
Derwent Abstract No. AN-94-299797 of Japanese Patent No. 6228183 (no date).

*Primary Examiner*—Arun S. Phasge
*Attorney, Agent, or Firm*—Dennis P. Tramaloni; Alan P. Kass; Bruce A. Pokras

[57] ABSTRACT

A process for the preparation of ascorbic acid starting from an ascorbate is characterized in that an ascorbate, e.g. sodium ascorbate, dissolved in water is decomposed under the influence of an electric field by means of ion-selective membranes into ascorbate ions and cations and the latter are separated spatially from one another and then, as a result of simultaneous generation of protons and hydroxide ions, the ascorbic acid is prepared from the liberated ascorbate ions and protons and, spatially separated therefrom, the corresponding hydroxide, e.g. sodium hydroxide, is also prepared from the cations and hydroxide ions.

16 Claims, 4 Drawing Sheets

PROCESS FOR MAKING ASCORBIC ACID

BACKGROUND OF THE INVENTION

The present invention comprises an electrophysical process for the preparation of ascorbic acid (vitamin C) from ascorbates.

Both electrodialysis with monopolar and bipolar membranes and electrolysis with monopolar and bipolar electrodes have been known for some time. For example, the use of electrodialysis with monopolar and/or bipolar membranes for obtaining organic acids is described in detail in the PCT Patent Publication WO 92/11080. However, said patent publication deals only with salts of carboxylic acids, in particular alkali metal formates (sodium formate) and alkali metal acetates. Furthermore, purification of ascorbic acid by means of electrodialysis is described in German Offenlegungsschrift 3 621 781. In this patent publication, salts are removed from the ascorbic acid which are formed by neutralization in the case of an acidic rearrangement in the ascorbic acid or which are present after liberation from the sodium ascorbate by means of acid in the case of an alkaline rearrangement. In both cases, a salt flow is obtained in addition to the ascorbic acid.

Hitherto, the conversion of sodium ascorbate to ascorbic acid was carried out on an industrial scale with the aid of ion exchanger resins. In this process, sodium ions are exchanged for protons present on the exchanger resin, and in this way the ascorbic acid is liberated from its salt. Once the capacity of the resin is exhausted, it has to be regenerated with acid, the acid having to be used in excess (not a stoichiometric process). In this process, an acidic salt solution which has subsequently to be neutralized and disposed of is formed as waste product, which results in additional expenditure and costs.

SUMMARY OF THE INVENTION

In the preparation process according to the invention, the ascorbate, preferably sodium ascorbate, dissolved in water is cleaved under the influence of an electric field into the corresponding cations (generally referred to as "counterions"), e.g., sodium ions ($Na^+$), and ascorbate ions ($Asc^-$). The oppositely charged ions are collected in a spatially separated manner in acid and base compartments (salt compartments) respectively which are bounded by ion-selective membranes. In the acid compartment, the ascorbate ions are combined in an ion reaction with protons ($H^+$) to form ascorbic acid (HAsc), while the counterions ($M^+$) are likewise combined in the base compartment with hydroxide ions ($OH^-$), which yields the corresponding base (MOH) as the second product of the ion reaction. The resulting aqueous solutions of ascorbic acid and base (hydroxide solution) can then be separately removed from the equipment in which the above-described electrophysical process takes place. The byproduct MOH, obtained together with the main product, ascorbic acid, is itself a useful material and can be used elsewhere.

In contrast to the prior art, the process according to the invention produces not only ascorbic acid, but also, spatially separated therefrom, the corresponding hydroxide, e.g., sodium hydroxide. In addition, salts are not formed in carrying out the process according to the invention.

DETAILED DESCRIPTION OF THE INVENTION

In accordance with the invention, an ascorbate, preferably sodium ascorbate, which has been dissolved in water is cleaved under the influence of an electric field into the corresponding cation and anion. The cation (which is also referred to as the "counterion") is, e.g., a sodium ion ($Na^+$), and the anion is an ascorbate ion ($Asc^-$). These oppositely charged ions are transferred in a spatially separated manner into acid and base compartments (salt compartments) respectively, which are bounded by ion-selective membranes.

In the acid compartment, the ascorbate ions are combined in an ion reaction with protons ($H^+$) to form ascorbic acid (HAsc). In the base compartment, the counterions ($M^+$) are combined with hydroxide ions ($OH^-$) to yield the corresponding base (MOH) as a second product. The resulting aqueous solutions of ascorbic acid and base (hydroxide solution) can then be separately removed from the equipment in which the above-described electrophysical process takes place. The byproduct MOH is itself a useful, rather than waste, material.

In the process of the invention which has, inter alia, various embodiments depending on the nature of the ion-selective membranes and the electrodes which have been used, the protons can in principle be made available in two different ways:

a) by an electrically induced water dissociation at a bipolar membrane, this being an electrodialysis, and b) from an electrolysis which takes place at a monopolar or bipolar electrode.

Accordingly, the present invention is directed to a process for the preparation of ascorbic acid starting from an ascorbate, preferably the sodium ascorbate, which is characterized in that the ascorbate dissolved in water is separated under the influence of an electric field by means of ion-selective membranes into ascorbate ions and cations. The ions are separated spatially from one another, and then, by simultaneous generation of protons and hydroxide ions by the splitting of water, the ascorbic acid is prepared from the ascorbate ions and protons and a hydroxide compound is also prepared from the cations and hydroxide ions. The ascorbic acid prepared in this way and, if desired the hydroxide, can then be isolated from their respective aqueous solutions by conventional means.

The process of the invention for the preparation of ascorbic acid from an ascorbic acid salt in an electrolytic cell having an anode and a cathode is preferably carried out by:

1) converting the ascorbic acid salt dissolved in water under the influence of an electric field disposed across the anode and cathode into an ascorbate anion and a salt cation;

2) separating the ascorbate anion and the salt cation by means of ion-selective membranes, whereby at least one of the ions migrates across an ion-selective membrane under the influence of the electric field into a second chamber in the electrolytic cell, while simultaneously generating protons and hydroxide ions by splitting water in the electric field;

3) allowing the ascorbate anion in one chamber to react with the proton obtained by the splitting of water to obtain ascorbic acid.

Figure 1:
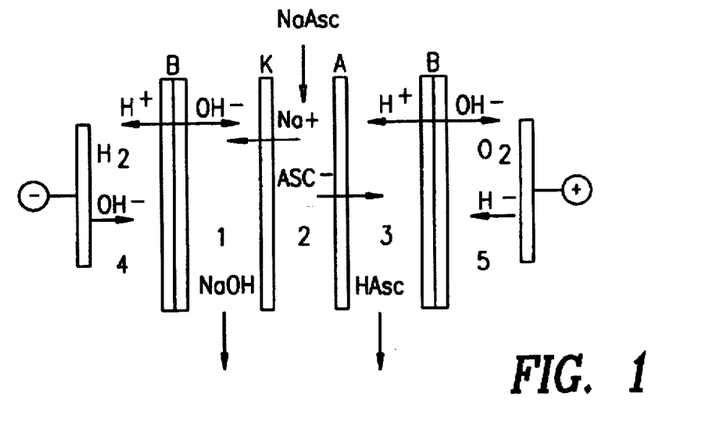
FIG. 1: Preparation of ascorbic acid from sodium ascorbate via electrodialysis using bipolar membranes in the three-chamber system.

The process of the invention may be carried out by any conventional means. The Figures herein illustrate several preferred embodiments. In the embodiment of FIG. 1, the process comprises making ascorbic acid from an ascorbic acid salt in an electrolytic cell having a cathode and anode and disposed therebetween:

1) a first bipolar ion exchange membrane adjacent to the anode which bipolar membrane comprises an anion exchange layer and a cation exchange layer with the anion exchange layer facing said anode whereby the bipolar membrane and the anode form an anode circulation compartment through which flows an aqueous salt solution, 2) an anion exchange membrane adjacent to the first bipolar ion exchange membrane whereby the bipolar ion exchange membrane and the anion exchange membrane form an ascorbic acid compartment in which there is formed an aqueous solution of the ascorbic acid, 3) a cation exchange membrane adjacent to the anion exchange membrane whereby the anion exchange membrane and the cation exchange membrane form an ascorbic acid salt compartment in which is introduced an aqueous solution of the ascorbic acid salt, 4) and a second bipolar ion exchange membrane adjacent to the cation exchange membrane which bipolar membrane comprises an anion exchange layer and a cation exchange layer with the cation exchange layer facing the cathode, whereby the cation exchange membrane and the second bipolar ion exchange membrane form a base compartment in which there is formed an aqueous base solution, and the second bipolar ion exchange membrane and the cathode form a cathode circulation compartment through which flows an aqueous salt solution;

wherein the ascorbic acid is produced from the ascorbic acid salt by:

1) applying a sufficient electrical potential across the cell to convert the ascorbic acid salt in the ascorbic acid salt compartment into an ascorbate anion and a salt cation and to simultaneously split water at the first and second bipolar membranes to produce OH⁻ in the base compartment and H⁺ in the ascorbic acid compartment;

2) separating the ascorbate anion from the salt cation under the influence of the electrical field, said electrical field causing the ascorbate anion to migrate toward the anode across the anion-selective membrane into the ascorbic acid compartment and causing the salt cation to migrate toward the cathode across the cation-selective membrane into the base compartment; and 3) allowing the ascorbate anion to react with the proton, simultaneously obtained by the splitting of water at the bipolar membrane in the ascorbic acid compartment in order to obtain ascorbic acid.

Figure 2:
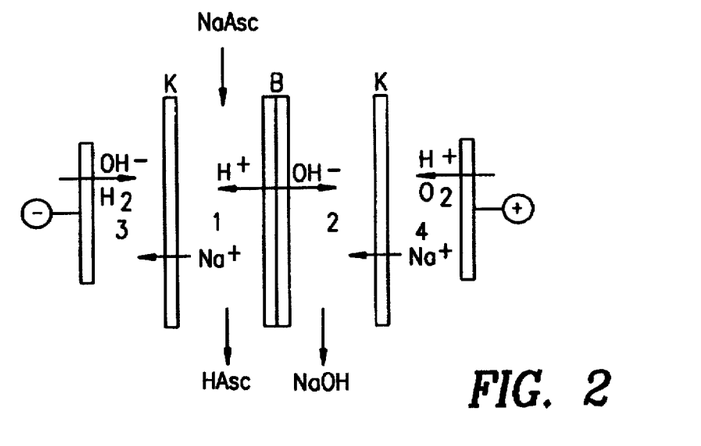
FIG. 2: Preparation of ascorbic acid from sodium ascorbate via electrodialysis using bipolar membranes in the two-chamber system.

In the embodiment of FIG. 2, the process comprises making ascorbic acid from an ascorbic acid salt in an electrolytic cell having a cathode and anode and disposed therebetween:

1) a first cation exchange membrane adjacent to the anode whereby the first cation exchange membrane and the anode form an anode circulation chamber through which flows an aqueous salt solution;

2) a bipolar ion exchange membrane adjacent to the first cation exchange membrane which bipolar membrane comprises an anion exchange layer and a cation exchange layer with the anion exchange layer facing said anode whereby the bipolar ion exchange membrane and the first cation exchange membrane form a base compartment in which there is formed an aqueous base solution;

3) a second cation exchange membrane adjacent to the bipolar membrane whereby the second cation exchange membrane and the bipolar membrane form an ascorbic acid salt/ascorbic acid compartment in which an aqueous solution of the ascorbic acid salt is introduced and the ascorbic acid is obtained from the ascorbic acid salt and the proton generated at the bipolar membrane, and the second cation exchange membrane and the cathode form a cathode circulation chamber through which flows an aqueous base solution;

wherein the ascorbic acid is produced from the ascorbic acid salt by:

1) applying a sufficient electrical potential across the cell to convert the ascorbic acid salt in the ascorbic acid salt/ascorbic acid compartment into an ascorbate anion and a salt cation and to split water at the bipolar membrane to produce OH⁻ in the base compartment and H⁺ in the ascorbic acid salt/ascorbic acid compartment;

2) separating the salt cation from the ascorbate anion under the influence of the electrical field, said electrical field causing the salt cation to migrate toward the cathode across the second cation exchange membrane into the cathode circulation compartment, and simultaneously transferring the salt cation from the anode circulation compartment into the base compartment;

3) allowing the ascorbate anion to react with the proton simultaneously obtained by the splitting of water at the bipolar membrane in the ascorbic acid salt/ascorbic acid compartment in order to obtain ascorbic acid.

Figure 3:
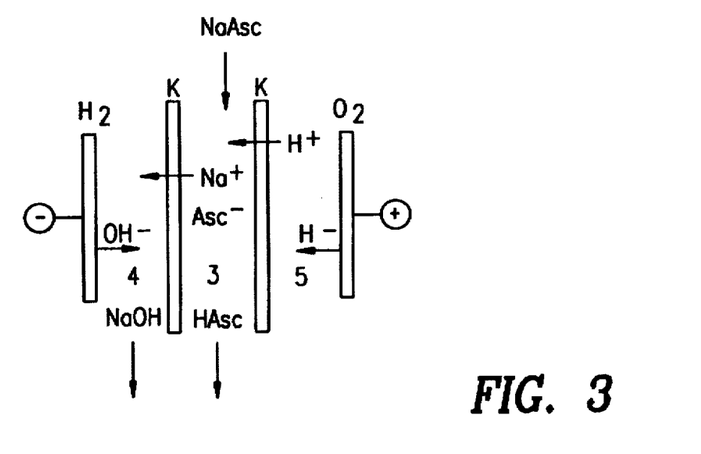
FIG. 3: Preparation of ascorbic acid from sodium ascorbate via electrolysis using monopolar electrodes in the three-chamber system.

In the embodiment of FIG. 3, the process comprises making ascorbic acid from an ascorbic acid salt in an electrolytic cell having a anode and cathode and disposed therebetween:

1) a first cation exchange membrane adjacent to the anode whereby the first cation exchange membrane and the anode form an anode circulation compartment through which flows an acid solution, 2) a second cation exchange membrane adjacent to first cation exchange membrane whereby the second cation exchange membrane and the first cation exchange membrane form an ascorbic acid salt/ascorbic acid compartment in which is introduced an aqueous solution of the ascorbic acid salt, and the ascorbic acid is obtained from the ascorbic acid salt by protonation, and the second cation exchange membrane and the cathode form a cathode circulation chamber through which flows an aqueous base solution;

wherein the ascorbic acid is produced from the ascorbic acid salt by:

1) applying a sufficient electrical potential across the cell to convert the ascorbic acid salt in the ascorbic acid salt/ascorbic acid compartment into an ascorbate anion and to simultaneously split water at both the cathode, to produce OH⁻ in the cathode circulation compartment, and at the anode, to produce H⁺ in anode circulation compartment;

2) separating the salt cation from the ascorbate anion under the influence of the electrical field, said electrical field causing the salt cation to migrate toward the cathode across the second cation exchange membrane into the cathode circulation compartment while simultaneously causing the $H^+$ in the anode circulation compartment to migrate across the first cation exchange membrane into the ascorbic acid salt/ascorbic acid compartment; and 3) allowing the ascorbate anion to react in the ascorbic acid salt/ascorbic acid compartment with the $H^+$ to obtain ascorbic acid.

Figure 4:
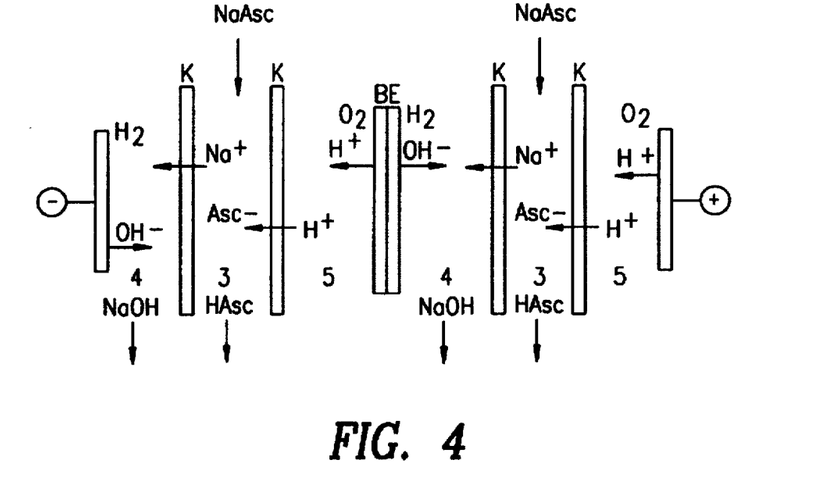
FIG. 4: Preparation of ascorbic acid from sodium ascorbate via electrolysis using monopolar membranes and bipolar electrodes (BE) in the three-chamber system.
Figure 5:
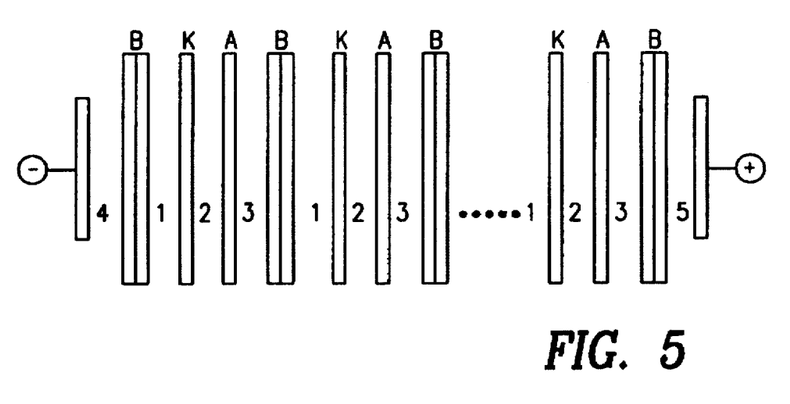
FIG. 5: Arrangement of a plurality of the three-chamber assemblies shown in FIG. 1.
Figure 6:
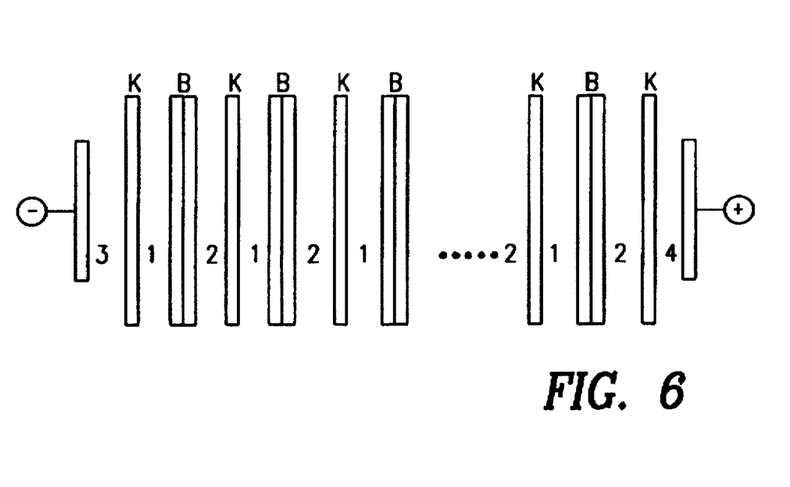
FIG. 6: Arrangement of a plurality of the two-chamber assemblies shown in FIG. 2.
Figure 7:
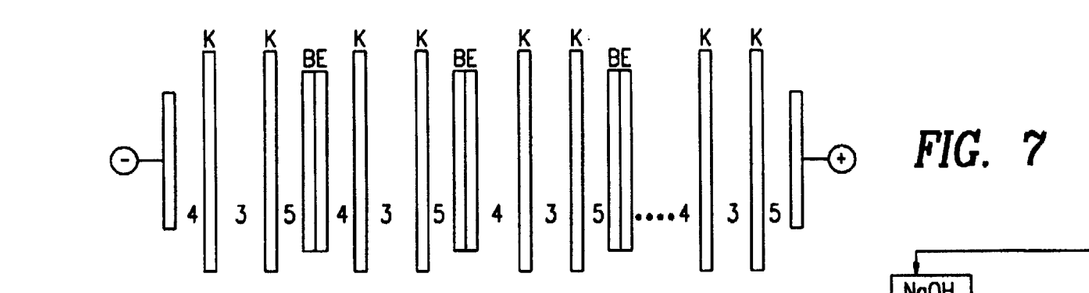
FIG. 7: Arrangement of a plurality of the three-chamber assemblies shown in FIG. 4.

As illustrated in FIG. 5, the process of FIG. 1 may be carried out with a plurality of the three-chamber assemblies of FIG. 1 disposed between a single cathode and a single anode. FIG. 6 illustrates how the process of FIG. 2 may be carried out with a plurality of the two-chamber assemblies of FIG. 2 disposed between a single cathode and single anode. FIG. 7 illustrates how the process of FIG. 4 may be carried out with a plurality of the three-chamber assemblies of FIG. 4 disposed between a single cathode and single anode.

FIG. 4 illustrates an arrangement where two complete assemblies of FIG. 3 are arranged side-by-side, except that the interior individual cathode and anode are replaced by a bipolar electrode.

As mentioned above, the process according to the invention can be carried out either with the use of electrodialysis or with the use of electrolysis.

The advantages of the invention described herein are that the ascorbates, preferably sodium ascorbate, are converted to ascorbic acid without the use of additional chemicals. Furthermore, hydroxide which can be used as a useful material elsewhere is obtained as a byproduct.

The spatial separation of the cations [for example sodium ions ($Na^+$)] and ascorbate ions ($Asc^-$) from one another as featured in the process according to the invention and, at the same time, embodiments of said process are shown in the figures herein, in which A denotes a (monopolar) anion exchanger membrane, B denotes a bipolar membrane and K denotes a cation exchanger membrane.

Electrodialysis using bipolar membranes can be carried out either in a three-chamber system (FIG. 1) or in a two-chamber system (FIG. 2).

If the protons are produced at an electrode, a three-chamber system is utilized (FIG. 3, FIG. 4).

In the cases shown in FIGS. 1, 2 and 4, a multiplicity of three-chamber assemblies or two-chamber assemblies can be arranged between an electrode pair, as shown in FIGS. 5, 6 and 7.

The invention is now explained in detail by reference to the above FIGS. 1 to 7.

FIG. 1: Preparation of ascorbic acid from sodium ascorbate with the aid of electrodialysis using bipolar membranes in the three-chamber system Sodium ions and ascorbate ions are removed under the influence of an electric field from the chamber 2 which has sodium ascorbate solution flowing through it, and spatially separated from one another with the aid of ion-selective membranes. In this process, the sodium ions migrate via a cation exchanger membrane in the direction of the cathode and consequently enter the base circuit 1 where they react with the hydroxide ions produced by a bipolar membrane to form sodium hydroxide. The ascorbate ions migrate via an anion exchanger membrane in the direction of the anode and consequently enter the acid circuit 3, where they react with the protons produced by a bipolar membrane to form ascorbic acid. The electrode circulation systems (chambers 4 and 5) have a salt or base solution flowing through them. Any conventional salt or base may be used in accordance with the current invention so long as it imparts sufficient electrical conductivity to the solution for carrying out the present process. Preferred salts are sodium and potassium sulfate. Preferred bases are sodium and potassium hydroxide. Dilute rather than concentrated solutions are preferred, especially in the range of 0.25 to 1.0 molar.

According to FIG. 5, any number of the above-described three-chamber assemblies (base, sodium ascorbate, ascorbic acid) can be arranged between an electrode pair.

FIG. 2: Preparation of ascorbic acid from sodium ascorbate with the aid of electrodialysis using bipolar membranes in the two-chamber system Sodium ions are removed under the influence of an electric field from the chamber 1 which has sodium ascorbate solution flowing through it. Electrical neutrality is maintained in the chamber 1 by every sodium ion being replaced or displaced by a proton produced by the bipolar membrane.

In this process the sodium ions migrate via a cation exchanger membrane in the direction of the cathode and consequently enter the base circuit 2, where they react with the hydroxide ions produced by a bipolar membrane to form sodium hydroxide. The ascorbate ions react in the acid circuit 1 with the protons produced by the bipolar membrane to form ascorbic acid. The electrode circulation systems (chambers 3 and 4) have a sodium hydroxide solution (chamber 3) or salt or base solution (chamber 4) flowing through them. Any conventional salt or base may be used in accordance with the current invention so long as it imparts sufficient electrical conductivity to the solution for carrying out the present process. Preferred salts are sodium and potassium sulfate. Preferred bases are sodium and potassium hydroxide. Dilute rather than concentrated solutions are preferred, especially in the range of 0.25 to 1.0 molar.

According to FIG. 6, any number of two-chamber assemblies (base, ascorbic acid) can be arranged between an electrode pair.

FIG. 3: Preparation of ascorbic acid from sodium ascorbate with the aid of electrolysis using monopolar electrodes in the three-chamber system Sodium ions are separated under the influence of an electric field from the chamber 3 which has sodium ascorbate solution flowing through it. Electrical neutrality is maintained in the chamber 3 by every sodium ion being replaced or displaced by a proton produced at the anode in the circuit 5. In this process, the sodium ions move under the influence of the electric field via a cation exchanger membrane in the direction of the cathode and consequently enter the base circuit 4, where they react with the hydroxide ions produced at the cathode to form sodium hydroxide. The ascorbate ions react in the acid circuit 3 with the protons produced at the anode to form ascorbic acid. The cathode circulation system (chamber 4) has the base produced flowing through it, while the anode circulation system (chamber 5) has an acid flowing through it. Any conventional acid may be used in accordance with the current invention so long as it imparts sufficient electrical conductivity to the solution for carrying out the present process. Preferred acids are the mineral acids, especially sulphuric acid. Dilute rather than concentrated solutions are preferred, especially in the range of 0.25 to 1.0 molar.

FIG. 4: Preparation of ascorbic acid from sodium ascorbate with the aid of electrolysis using monopolar membranes and bipolar electrodes in the three-chamber system Sodium ions are separated under the influence of an electric field from the chamber 3 which has sodium ascorbate solution flowing through it. Electrical neutrality is maintained in the chamber 3 by every sodium ion being replaced or displaced by a proton produced at the anode of the bipolar electrode (BE) or monopolar electrode in the circuit 5. In this process, the protons produced enter the acid chamber 3 under the influence of the electric field via a cation exchanger membrane. The sodium ions migrate via a cation exchanger membrane in the direction of the cathode and consequently enter the base circuit 4, where they react with the hydroxide ions produced at the cathode of the bipolar electrode (BE) or monopolar electrode to form sodium hydroxide. The ascorbate ions react in the acid circuit 3 with the protons produced at the anode to form ascorbic acid. The cathode circulation system (chamber 4) has the base produced flowing through it, while the anode circulation system (chamber 5) has an acid flowing through it. Any conventional acid may be used in accordance with the current invention so long as it imparts sufficient electrical conductivity to the solution for carrying out the present process. Preferred acids are the mineral acids, especially sulphuric acid. Dilute rather than concentrated solutions are preferred, especially in the range of 0.25 to 1.0 molar.

According to FIG. 7, any number of three-chamber assemblies (base, ascorbic acid, acid) can be arranged between an electrode pair.

Within the scope of the present invention, unless specifically restricted to sodium ascorbate, the term "ascorbate" is to be understood as meaning, in particular, an alkali metal ($M^+$) ascorbate or a tertiary ammonium ($HNR_3+$) ascorbate or a quaternary ammonium ($NR_4+$) ascorbate, where $M^+$ stands, in particular, for the lithium, sodium or potassium ion and every R of the ion $HNR_3+$ or $NR_4+$ stands, in particular, for a straight-chain or branched alkyl group, in particular a lower alkyl group, e.g. $C_{1-4}$-alkyl group, preferably methyl. Sodium ascorbate is preferably used as the ascorbate.

The aqueous ascorbate solution used in the process according to the invention has a concentration which is in general in the range from about 15 to about 45 weight/weight-% (w/w-%) relative to the solution, preferably in the range from about 25 to about 35 w/w-%. In any case, with account being taken of the nature of the cation and the other process conditions, e.g. the temperature, the concentration must be chosen so that if possible the ascorbate does not crystallize out of the solution.

Both an anion or cation exchanger membrane (monopolar membrane) and a bipolar membrane are suitable as ion-selective membrane for use in the process according to the invention. The anion exchanger membranes ("A" in the relevant figures) are in general strongly, mildly or weakly basic membranes which are selective for and permeable to monovalent anions, but not monovalent cations. Examples of such membranes are the Selemion® ASV, AMV, AAV and ASV membranes supplied by Asahi Glass K. K., Japan, the Neosepta ACS membrane supplied by Tokuyama Soda K. K., also in Japan, and also some supplied by Ionics Inc., Watertown, Mass., USA, in particular the Ionics 204-UZL-386 membrane supplied by this company. The cation exchanger membranes ("K" in the relevant figures) are, on the other hand, mildly or strongly acidic membranes which contain, for example, phosphoric acid groups or sulphonic acid groups, are permselective and have a low electrical resistance at the pH used. In addition, they allow monovalent cations through, but no monovalent anions. Relevant examples are the CMX membrane and the CMB membrane of Tokuyama Soda K. K., the CMV membrane of Asahi Glass K. K., the Nafion® 110, 324, 350 and 450 membranes supplied by DuPont de Nemours, USA and also the cation exchanger membranes described in U.S. Pat. No. 4,738,764 (Chlanda et al.). The bipolar membranes ("B" in the relevant figures) have a cation (+) layer and an anion (−) layer, the former being permeable to monovalent cations and the latter to monovalent anions. In addition, the cation layer does not allow any anions through and the anion layer does not allow any cations through. Examples of bipolar membranes are the WSI membrane supplied by WSI Technologies Inc., St. Louis, Mo., USA, the FBI membrane supplied by FuMa-Tech, Germany, and also the bipolar membranes described in U.S. Pat. Nos. 2,829,095, 4,024,043, 4,082,835 and 4,116,889.

The ideal current density or electric voltage at which the process according to the invention is carried out depends in each case on many other parameters, e.g. the concentration of the aqueous ascorbate solution, the type and number of membranes used and in general on their arrangement and dimensions (inter alia, chamber thickness, i.e. the distance of the membranes from one another) and also the temperature at which the process is carried out, so that the limiting values cannot easily be determined, if at all. As a consequence of past investigations of the process according to the invention, it can, however, be established that the current density is appropriately in the range from about 50 to about 200 mA/cm$^2$. In practice, it proves to be useful to vary the current density while measuring the rate of production of the ascorbic acid until an optimum process pattern has been established.

Since ascorbic acid is markedly sensitive to heat and starts to decompose even at temperatures which are not excessively elevated, from about 40° C. upwards, the process according to the invention is expediently carried out at temperatures below about 40° C., but also above about 10° C. for economic reasons. Preferably, the process is carried out within the range from about 15° C. up to about 25° C.

In addition, the process according to the invention has a plurality of preferred embodiments in relation to the nature and arrangement of the membranes and electrodes used, while using, for example, the preferred ascorbate sodium ascorbate, and to be precise:

(i) The process is carried out in such a way that the protons and hydroxide ions are liberated by an electrically induced water dissociation at a bipolar membrane and then react with the ascorbate ions and the sodium ions to form ascorbic acid and sodium hydroxide, respectively, while spatially separated from one another. This embodiment is an electrodialysis, such as that which can be illustrated, for example, by FIGS. 1 and 2 (still more specifically, FIGS. 5 and 6) provided above and the pertinent explanations. Preferably, this embodiment of the process according to the invention is carried out in such a way that a plurality of three-chamber assemblies each comprising a base chamber, a sodium ascorbate chamber and an ascorbic acid chamber are arranged behind one another between an electrode pair, such as that which can be seen, for example, from FIG. 5.

(ii) The process is carried out in such a way that the sodium ions of the sodium ascorbate in the aqueous solution are replaced or displaced by the protons liberated as a consequence of an electrically induced water dissociation at a bipolar membrane and are transported under the influence of the electric field via a cation exchanger membrane into the adjacent circuit, where they react with the hydroxide ions produced at the bipolar membrane to form sodium hydroxide. This embodiment is also an electrodialysis, such as that which can be illustrated, for example, by FIG. 2 and the pertinent explanation. Preferably, this embodiment of the process according to the invention is carried out in such a way that a plurality of two-chamber assemblies each comprising a base chamber and an ascorbic acid chamber are arranged behind one another between an electrode pair, as can be seen, for example, from FIG. 6.

(iii) The process is carried out in such a way that the sodium ions of the sodium ascorbate in the aqueous solution are replaced or displaced by the protons liberated at a bipolar electrode and react with the hydroxide ions liberated at the bipolar electrode to form sodium hydroxide in a chamber separated by a cation exchanger membrane. This embodiment is an electrolysis, such as that which can be illustrated, for example, by FIG. 4 provided above and the pertinent explanation. Preferably, this embodiment of the process according to the invention is carried out in such a way that a plurality of three-chamber assemblies each comprising a base chamber, an ascorbic acid chamber and an acid chamber are arranged behind one another between a monopolar electrode pair, such as that which can be seen, for example, from FIG. 7.

The present invention is illustrated by the Example below:

EXAMPLE

Performance of the electrodialysis

Approximately 300 g of sodium ascorbate were dissolved in deionized water, resulting ultimately in an approximately 30 w/w-% sodium ascorbate solution. This was transferred to circuit 1 (see FIG. 8 below) and pumped round (approximately 30 l/h) at a current strength of 5 A. The conversion was carried out until the conductivity in the product circuit had dropped to about 1.7 to 2.2 mS/cm. The electrode circulation circuit 2 was operated (approximately 40 l/h) with a 0.1 molar sodium hydroxide solution. The sodium hydroxide circuit 3 was started (approximately 20 l/h) with a conductivity of 20 mS/cm. The circuits 1 to 3 were cooled by an external cooling circuit.

A total of approximately 200 electrodialyses were carried out with crude sodium ascorbate in this manner, the amount of sodium ascorbate used being in the range from approximately 270 to 350 g per batch.

After reaching a final conductivity of approximately 2 mS/cm, the electrodialysis is terminated and the aqueous ascorbic acid solution (approximately 22–25 w/w-%) is removed from the circuit 1 (container) and processed further.

After removal of residual sodium ions (approximately 500 ppm) and standard processing, ascorbic acid complying in each case with the specifications was isolated.

Data relating to the electrodialysis module

The electrodialysis was carried out with a commercial module (two-chamber system) supplied by the company GOEMA (Vaihingen/Enz, Germany). The chamber thickness was 2 mm and the module was equipped with 4 pairs of cells having a membrane area of 36 cm$^2$ in each case (=144 cm$^2$ total area). As the membranes, a CMX membrane (Tokuyama Soda Co. Ltd. Japan) was used as the cation exchanger membrane and a WSI membrane or a FBI membrane (WSI Technologies Inc., St. Louis, Mo. USA or FuMa-Tech, Germany, respectively) was used as the bipolar membrane. Mixed metal oxide electrodes were used as electrodes.

Other data

Current strength: 5.0 amperes (constant)

Voltage: 28 to 44 volts

Membrane area: 144 cm$^2$

Production rate: 120 to 128 g Asc/h

Recovery: 98.5 to 99.5% (relative to ascorbate)

Residual Na (in Asc): approximately 500 ppm (average value)

The current efficiencies were in the range from 92 to 98%, predominantly 95%.

Figure 8:
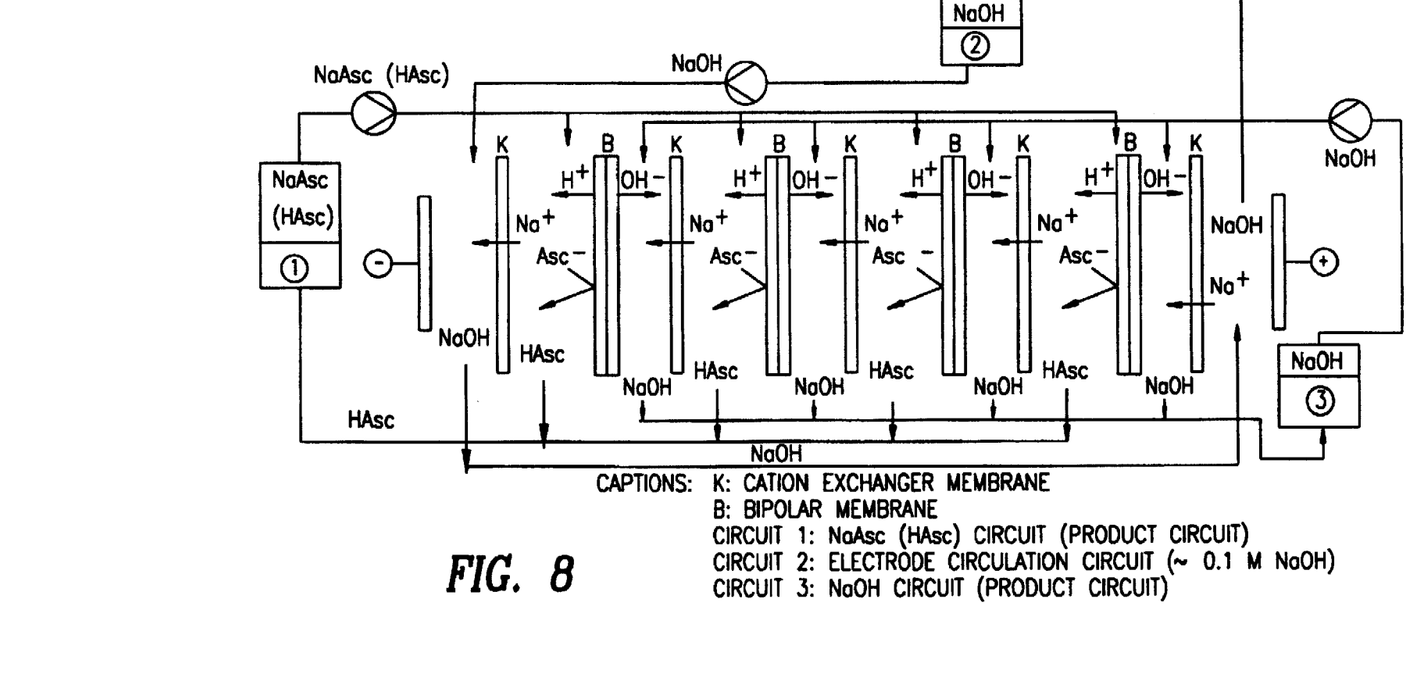
FIG. 8: Electrodialysis unit comprising 4 pairs of cells.

Shown in FIG. 8 is a drawing of the electrodialysis equipment with which the conversion of sodium ascorbate into ascorbic acid was carried out. A tabular overview with measured values (voltage, conductivity) as a function of time is given below for an electrodialysis of sodium ascorbate:

| Time [min] | Voltage [V] | Conductivity [mS/cm] |
|---|---|---|
| 0 | 30.5 | 25.6 |
| 4 | 30.0 | 23.0 |
| 8 | 29.5 | 22.1 |
| 12 | 29.2 | 21.5 |
| 16 | 28.8 | 21.1 |
| 20 | 28.7 | 20.6 |
| 24 | 28.4 | 20.2 |
| 28 | 28.3 | 19.7 |
| 32 | 28.1 | 19.2 |
| 36 | 28.0 | 18.6 |
| 40 | 27.8 | 18.2 |
| 44 | 27.8 | 17.5 |
| 48 | 27.6 | 17.0 |
| 52 | 27.9 | 16.4 |
| 56 | 27.9 | 15.7 |
| 60 | 27.9 | 15.1 |
| 64 | 29.4 | 14.4 |
| 68 | 29.4 | 13.9 |
| 72 | 29.6 | 13.2 |
| 76 | 29.6 | 12.2 |
| 80 | 29.7 | 11.6 |
| 84 | 30.0 | 10.9 |
| 88 | 30.6 | 10.0 |
| 92 | 30.8 | 9.2 |
| 96 | 31.2 | 8.4 |
| 100 | 32.0 | 7.3 |
| 104 | 33.0 | 6.5 |
| 108 | 33.8 | 5.7 |
| 112 | 35.4 | 4.9 |
| 116 | 37.0 | 4.1 |
| 120 | 39.8 | 3.4 |
| 124 | 42.0 | 2.7 |
| 128 | 43.8 | 2.2 |
| 132 | 44.0 | 1.9 |
| 136 | 43.8 | 1.8 |

Figure 9:
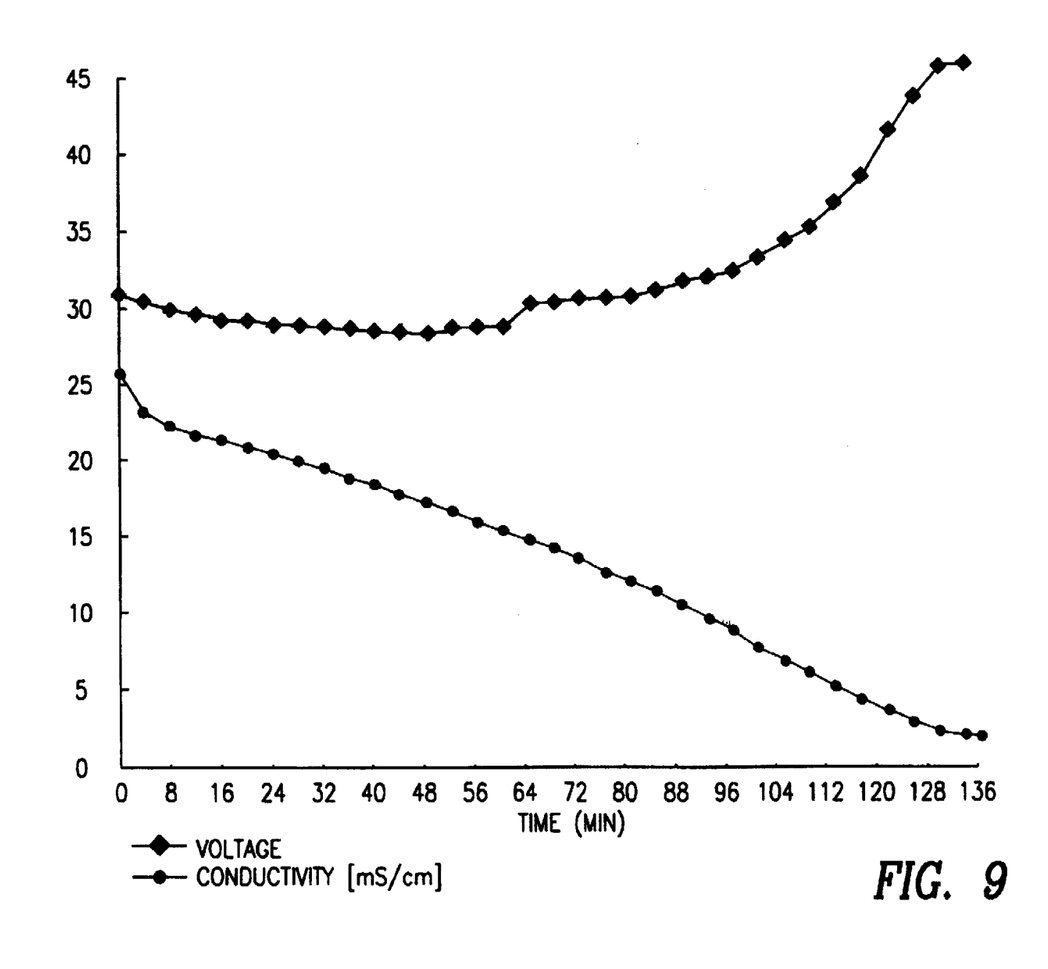
FIG. 9: A representative graph of electrodialysis.

A representative graphical pattern of an electrodialysis is presented in FIG. 9. The voltage and conductivity were plotted against time.

I claim:

1. A process for the preparation of ascorbic acid from an ascorbic acid salt in an electrolytic cell having an anode and a cathode, comprising:

1) converting the ascorbic acid salt dissolved in water under the influence of an electric field disposed across the anode and cathode into an ascorbate anion and a salt cation;

2) separating the ascorbate anion and the salt cation by means of ion-selective membranes, whereby at least one of the ions migrates across an ion-selective membrane under the influence of the electric field into a second chamber in the electrolytic cell, while simultaneously generating protons and hydroxide ions by splitting water in the electric field;

3) allowing the ascorbate anion in one chamber to react with the proton obtained by the splitting of water to obtain ascorbic acid.

2. The process of claim 1 which process comprises making ascorbic acid from an ascorbic acid salt in an electrolytic cell having a cathode and anode and disposed therebetween:

1) a first bipolar ion exchange membrane adjacent to the anode which bipolar membrane comprises an anion exchange layer and a cation exchange layer with the anion exchange layer facing said anode whereby the bipolar membrane and the anode form an anode circulation compartment through which flows an aqueous salt solution, 2) an anion exchange membrane adjacent to the first bipolar ion exchange membrane whereby the bipolar ion exchange membrane and the anion exchange membrane form an ascorbic acid compartment in which there is formed an aqueous solution of the ascorbic acid, 3) a cation exchange membrane adjacent to the anion exchange membrane whereby the anion exchange membrane and the cation exchange membrane form an ascorbic acid salt compartment in which is introduced an aqueous solution of the ascorbic acid salt, 4) and a second bipolar ion exchange membrane adjacent to the cation exchange membrane which bipolar membrane comprises an anion exchange layer and a cation exchange layer with the cation exchange layer facing the cathode, whereby the cation exchange membrane and the second bipolar ion exchange membrane form a base compartment in which there is formed an aqueous base solution, and the second bipolar ion exchange membrane and the cathode form a cathode circulation compartment through which flows an aqueous salt solution;

wherein the ascorbic acid is produced from the ascorbic acid salt by:

1) applying a sufficient electrical potential across the cell to convert the ascorbic acid salt in the ascorbic acid salt compartment into an ascorbate anion and a salt cation and to simultaneously split water at the first and second bipolar membranes to produce $OH^-$ in the base compartment and $H^+$ in the ascorbic acid compartment;

2) separating the ascorbate anion from the salt cation under the influence of the electrical field, said electrical field causing the ascorbate anion to migrate toward the anode across the anion-selective membrane into the ascorbic acid compartment and causing the salt cation to migrate toward the cathode across the cation-selective membrane into the base compartment; and 3) allowing the ascorbate anion to react with the proton, simultaneously obtained by the splitting of water at the bipolar membrane in the ascorbic acid compartment in order to obtain ascorbic acid.

3. The process of claim 2 wherein the ascorbic acid salt is sodium ascorbate.

4. The process of claim 3 wherein the aqueous ascorbic acid salt solution has a concentration of the ascorbic acid salt in the range from about 15% to about 45% by weight of the solution.

5. The process of claim 4 wherein the aqueous ascorbic acid salt solution has a concentration of the ascorbic acid salt in the range from about 25% to about 35% by weight of the solution.

6. The process of claim 5 wherein the electrolytic cell comprises a plurality of three-chamber assemblies, each assembly comprising the base chamber, the sodium ascorbate chamber and the ascorbic acid chamber, disposed between the cathode circulation chamber and the anode circulation chamber.

7. The process of claim 1 which process comprises making ascorbic acid from an ascorbic acid salt in an electrolytic cell having a cathode and anode and disposed therebetween:

1) a first cation exchange membrane adjacent to the anode whereby the first cation exchange membrane and the anode form an anode circulation chamber through which flows an aqueous salt solution;

2) a bipolar ion exchange membrane adjacent to the first cation exchange membrane which bipolar membrane comprises an anion exchange layer and a cation exchange layer with the cation exchange layer facing said anode whereby the bipolar ion exchange membrane and the first cation exchange membrane form a base compartment in which there is formed an aqueous base solution;

3) a second cation exchange membrane adjacent to the bipolar membrane whereby the second cation exchange membrane and the bipolar membrane form an ascorbic acid salt/ascorbic acid compartment in which an aqueous solution of the ascorbic acid salt is introduced and the ascorbic acid is obtained from the ascorbic acid salt and the proton generated at the bipolar membrane, and the second cation exchange membrane and the cathode form a cathode circulation chamber through which flows an aqueous base solution;

wherein the ascorbic acid is produced from the ascorbic acid salt by:

1) applying a sufficient electrical potential across the cell to convert the ascorbic acid salt in the ascorbic acid salt/ascorbic acid compartment into an ascorbate anion and a salt cation and to split water at the bipolar membrane to produce $OH^-$ in the base compartment and $H^+$ in the ascorbic acid salt/ascorbic acid compartment;

2) separating the salt cation from the ascorbate anion under the influence of the electrical field, said electrical field causing the salt cation to migrate toward the cathode across the second cation exchange membrane into the cathode circulation compartment, and simultaneously transferring the salt cation from the anode circulation compartment into the base compartment;

3) allowing the ascorbate anion to react with the proton, simultaneously obtained by the splitting of water at the bipolar membrane in the ascorbic acid salt/ascorbic acid compartment in order to obtain ascorbic acid.

8. The process of claim 7 wherein the ascorbic acid salt is sodium ascorbate.

9. The process of claim 8 wherein the aqueous ascorbic acid salt solution has a concentration of the ascorbic acid salt in the range from about 15% to about 45% by weight of the solution.

10. The process of claim 9 wherein the aqueous ascorbic acid salt solution has a concentration of the ascorbic acid salt in the range from about 25% to about 35% by weight of the solution.

11. The process of claim 10 wherein the electrolytic cell comprises a plurality of two-chamber assemblies, each assembly comprising the base compartment and the ascorbate acid salt/ascorbic acid compartment, disposed between the cathode circulation chamber and the anode circulation chamber.

12. The process of claim 1 which process comprises making ascorbic acid from an ascorbic acid salt in an electrolytic cell having a anode and cathode and disposed therebetween:

1) a first cation exchange membrane adjacent to the anode whereby the first cation exchange membrane and the anode form an anode circulation compartment through which flows an acid solution, 2) a second cation exchange membrane adjacent to first cation exchange membrane whereby the second cation exchange membrane and the first cation exchange membrane form an ascorbic acid salt/ascorbic acid compartment in which is introduced an aqueous solution of the ascorbic acid salt, and the ascorbic acid is obtained from the ascorbic acid salt by protonation, and the second cation exchange membrane and the cathode form a cathode circulation chamber through which flows an aqueous base solution;

wherein the ascorbic acid is produced from the ascorbic acid salt by:

1) applying a sufficient electrical potential across the cell to convert the ascorbic acid salt in the ascorbic acid salt/ascorbic acid compartment into an ascorbate anion and to simultaneously split water at both the cathode, to produce $OH^-$ in the cathode circulation compartment, and at the anode, to produce $H^+$ in anode circulation compartment;

2) separating the salt cation from the ascorbate anion under the influence of the electrical field, said electrical field causing the salt cation to migrate toward the cathode across the second cation exchange membrane into the cathode circulation compartment while simultaneously causing the $H^+$ in the anode circulation compartment to migrate across the first cation exchange membrane into the ascorbic acid salt/ascorbic acid compartment; and 3) allowing the ascorbate anion to react in the ascorbic acid salt/ascorbic acid compartment with the $H^+$ to obtain ascorbic acid.

13. The process of claim 12 wherein the ascorbic acid salt is sodium ascorbate.

14. The process of claim 13 wherein the aqueous ascorbic acid salt solution has a concentration of the ascorbic acid salt in the range from about 15% to about 45% by weight of the solution.

15. The process of claim 14 wherein the aqueous ascorbic acid salt solution has a concentration of the ascorbic acid salt in the range from about 25% to about 35% by weight of the solution.

16. The process of claim 15 wherein the electrolytic cell comprises two three-chamber assemblies, said first assemby comprising an anode, a first acid compartment, a first ascorbate acid salt/ascorbic acid compartment and a first base compartment, and said second assembly comprising a second acid compartment, a second ascorbate acid salt/ascorbic acid compartment, a second base compartment and a cathode, wherein the first base compartment and the second acid compartment are separated by a bipolar electrode disposed between.

* * * * *